United States Patent [19]

Riefling

[11] Patent Number: 4,788,299

[45] Date of Patent: Nov. 29, 1988

[54] KETOLACTONES

[75] Inventor: Bernhard Riefling, Darmstadt, Fed. Rep. of Germany

[73] Assignee: Merck Patent Gesellschaft Mit Beschränkter Haftung, Darmstadt, Fed. Rep. of Germany

[21] Appl. No.: 63,044

[22] Filed: Jun. 17, 1987

[30] Foreign Application Priority Data

Jun. 18, 1986 [DE] Fed. Rep. of Germany ....... 3620442

[51] Int. Cl.$^4$ ................. C07D 307/93; C07D 307/935
[52] U.S. Cl. ..................................... 549/300; 549/305; 549/304
[58] Field of Search ......................... 549/305, 300, 304

[56] References Cited

U.S. PATENT DOCUMENTS

| | | | |
|---|---|---|---|
| 3,823,138 | 7/1974 | Van Rheenen | 549/214 |
| 4,103,091 | 7/1978 | Mitscher et al. | 549/312 |
| 4,472,428 | 9/1984 | Toru et al. | 549/305 |
| 4,622,410 | 11/1986 | Hamanaka et al. | 549/305 |
| 4,680,288 | 7/1987 | Irmscher et al. | 546/342 |

OTHER PUBLICATIONS

Chemical Abstracts, vol. 104, No. 26, Abstract 224,777n, Jun. 1986.

*Primary Examiner*—Alan L. Rotman
*Assistant Examiner*—Zinna Northington
*Attorney, Agent, or Firm*—Millen & White

[57] ABSTRACT

New ketolactones of the formula I

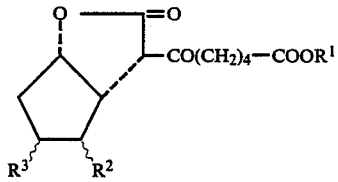

wherein
R$^1$ is H, alkyl having 1-6 C atoms or aryl having 6-14 C atoms and
R$^2$ and R$^3$ together are an O atom or together are a bond,
and salts thereof,
can be used as intermediate products in the preparation of prostaglandin derivatives.

7 Claims, No Drawings

KETOLACTONES

BACKGROUND OF THE INVENTION

The invention relates to new ketolactones and to salts thereof, and to a process for their preparation.

The synthesis of heptanoic acids such as 6-oxo-7-(2-$R^2$-3-$R^3$-5α-hydroxycyclopentyl)-heptanoic acids useful in the preparation of prostanoic acid derivatives (wherein $R^2$ and $R^3$ are defined below) hitherto known exhibits considerable disadvantages. Thus it proceeds via a large number of stages, in which unstable intermediate products are formed. One of these stages is a reduction using diisobutylaluminum hydride, an expensive reagent and one which is difficult to handle on an industrial scale.

SUMMARY OF THE INVENTION

It is therefore an object of this invention to find a new process and new intermediate products for the preparation of 6-oxo-7-(2-$R^2$-3-$R^3$-5α-hydroxycyclopentyl)-heptanoic acids and related compounds and hence for the preparation of prostaglandin derivatives, which do not have the disadvantages of the known process, or have them only to a lesser extent, and, in particular, are suitable for large industrial scale processes.

Upon further study of the specification and appended claims, further objects and advantages of this invention will become apparent to those skilled in the These objects have been achieved by the provision of new ketolactones of the formula I

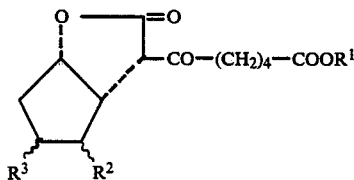

wherein
$R^1$ is H, alkyl having 1–6 C atoms or aryl having 6–14 C atoms and
$R^2$ and $R^3$ together are an O atom or together are a bond, and their salts.

These objects are further satisfied by the provision of a process for the preparation of said ketolactones characterized in that a lactone of the formula II

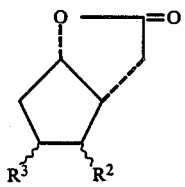

wherein
$R^2$ and $R^3$ have the meaning indicated, is reacted with and adipic acid ester-halide of the formula III

Hal—CO—(CH$_2$)$_4$—COOR$^4$   III wherein $R^4$ is alkyl having 1–6 C atoms or aryl having 6–14 C atoms and
Hal is Cl or Br, and/or a compound of the formula I ($R^2+R^3$=a bond) is converted into a compound of the formula I ($R^2+R^3$=O) by treatment with an oxidizing agent and/or a compound of the formula I ($R^1=R^4$) is saponified to give a compound of the formula I ($R^1$=H) and/or a compound of the formula I ($R^1$=H) is esterified or converted into one of its salts by treatment with a base.

DETAILED DISCUSSION

The compounds of the formula I can be used as intermediate products in the preparation of prostaglandin derivatives. In particular, it is possible, by treatment with bases, for example BaO in an aqueous medium, to obtain, by saponification, cleavage of the lactone ring and decarboxylation, 6—oxo—7—(2-$R^2$-3-$R^3$-5α-hydroxycyclopentyl)-heptanoic acids (IV) the conversion of which into certain 6-oxo-13-thia-prostanoic acid derivatives is described in German Offenlegungsschrift No. 3,401,542, which is equivalent to allowed U.S. application Ser. No. 692,490. These derivatives may be used as, e.g., hypotensives, inotropics and platelet aggregation inhibitors.

The new synthesis of IV, which proceeds via the ketolactone I, has fewer stages than the synthesis hitherto known, proceeds via more stable intermediate products and permits the use of cheaper reagents.

In the compounds of the formulae I and III, $R^1$ is preferably H, methyl or ethyl, and $R^4$ is preferably methyl or ethyl. Both radicals are also preferably propyl, isopropyl, butyl, isobutyl, sec-butyl, tertbutyl, pentyl, isopentyl, hexyl, isohexyl, phenyl, o-, m- or p-tolyl, o-, m- or p-fluorophenyl, o-, m- or p-chlorophenyl, o-, m- or p-methoxyphenyl, o-, m- or p-acetamidophenyl, or o-, m- or, especially, p-benzamidophenyl.

The starting materials of the formulae II and III are for the most part known. Insofar as they are not known, they can be prepared by known methods analogously to known compounds. Ihe lactones of formula 11 are, f.e., known from Tetrahedron Letters 1970(4), 311–313.

The preparation of the compounds of the formula I is, moreover, effected analogously to methods which are in themselves known, such as are described in the literature (for example in the standard works such as Houben-Weyl, Methoden der Organischen Chemie ("Methods of Organic Chemistry"), Georg-Thieme-Verlag, Stuttgart; or Organic Reactions, John Wiley & Sons, Inc., New York), specifically under reaction conditions such as are known and suitable for the reaction mentioned. In this regard it is also possible to make use of variants which are in themselves known but are not mentioned here in detail.

If desired, the starting materials of the formulae II and III can also be formed in situ by a process in which they are not isolated from the reaction mixture, but are immediately reacted further to give the compounds of the formula I.

Before being reacted with III, the lactone II is preferably converted into the corresponding anion by treatment with a base in an inert solvent. Examples of suitable bases are organometallic compounds, such as butyllithium, or alkali metal amides, such as NaNH$_2$, KNH$_2$ or a bis-(trimethylsilyl)-alkali metal amide, and examples of suitable solvents are ethers, such as tetrahydrofuran (THF), diethyl ether, diisopropyl ether, methyl tertbutyl ether or dioxane; the reaction temperatures are preferably between about −40° and +20°, preferentially between −30° and +10°. It is then preferable to add to the resulting solution a solution of III in an inert solvent, for example one of the solvents mentioned, the reaction temperatures being preferably between −80° and +30°.

A cyclopentene derivative I ($R^2+R^3$=a bond) can, if desired, be oxidized to give the corresponding epoxide I ($R^2+R^3$=O). Suitable oxidizing agents are, in particular, peroxides and hydroperoxides, such as peracetic acid, m-chloroperbenzoic acid or tertbutyl hydroperoxide. Hydroperoxides are preferably used in the presence of a catalyst, for example a heavy metal catalyst, such as molybdenum hexacarbonyl, vanadium(IV)oxide or a derivative thereof, for example vanadium(IV) oxideacetyl-acetonate. The oxidation is preferably carried out in the presence of an inert solvent, for example a carboxylic acid, such as acetic acid, a halogenated hydrocarbon, such as methylene dichloride, chloroform, carbontetrachloride, trichloroethylene, or an aromatic hydrocarbon, such as benzene or toluene, at temperatures between about 0° and 40° preferably between 15° and 30°. It is also possible to carry out the oxidation in several stages, for example by adding HOBr to give the bromohydrin and subsequently dehydrobrominating the product to give the epoxide.

An ester of the formula I ($R^1=R^4$) can be saponified to give the corresponding acid I ($R^1=H$), preferably under the customary mild alkaline or acid conditions, for example using aqueous or aqueous alcoholic solutions of NaOH or KOH at temperatures between 0 and 40°. In the course of this saponification the lactone ring is opened at the same time; it can be re-cyclized by subsequent brief treatment with an acid, for example hydrochloric acid. Under more vigorous conditions, for example using aqueous or aqueous alcoholic solutions or suspensions of alkali metal or alkaline earth metal hydroxides or oxides, such as BaO, at higher temperatures, for instance between 50 and 100°, decarboxylation also takes place and the compounds IV mentioned above are formed.

If desired, an acid of the formula I ($R^1=H$) or one of its reactive derivatives can be esterified in a customary manner with an alcohol or phenol of the formula $R^4$-OH or one of its reactive derivatives, for example in the presence of a strong acid, such as HCl or $H_2SO_4$, or a dehydrating agent, such as dicyclohexylcarbodiimide, it being preferable to carry out the reaction in an excess of the compound of the formula $R^4$-OH and/or in the presence of an inert solvent, at temperatures between 0° and 40°.

An acid of the formula I ($R^1=H$) can be converted into one of its metal or ammonium salts by reaction with a base. Suitable salts are, in particular, the sodium, potassium, magnesium, calcium and ammonium salts.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

"Customary working up" means as follows: if necessary, water is added, the mixture is extracted with methylene dichloride or ethyl acetate, the phases are separated, the organic phase is washed with water, dried over sodium sulfate and evaporated and the resulting crude product is purified by chromatography over silica gel.

The entire text of all applications, patents and publications, if any, cited above and below are hereby incorporated by reference.

EXAMPLES

Example 1

A solution of 3.4 ml of diisopropylamine in 10 ml of THF is cooled to 0° under nitrogen, and 14.5 ml of a 1.5-molar solution of butyllithium are added. The mixture is stirred for a further 30 minutes and is then cooled to −78° and a solution of 1.54 g of 2-oxa-1$\beta$H,5$\beta$H-bicyclo-[3,3,0]oct-6-en-3-one in 5 ml of THF is added dropwise slowly. After a further 30 minutes, this mixture is added dropwise to a solution, cooled in a bath of solid carbon dioxide, of 2.15 g of methyl 5-chlorocarbonyl-valerate in 10 ml of THF. The mixture is stirred for a further 30 minutes and 30 ml of a saturated aqueous solution of citric acid are then poured in. Customary working up gives 2-oxa-4-(5-methoxycarbonylpentanoyl)-1$\beta$H,5$\beta$H-bicyclo[3,3,0]oct-6-en-3-one (Ia) in the form of a yellowish oil. Mass spectrum: m/e=266.

Example 2

A solution of 1.61 g of 2-oxa-6$\alpha$,7$\alpha$-epoxy-1$\beta$H,5$\beta$H-bicyclo[3,3,0]octan-3-one in 10 ml of THF is added dropwise to a mixture, cooled to minus 30°, of 20 ml of 1-molar bis-(trimethylsilyl)-lithium amide/THF solution and 20 ml of THF. The mixture is stirred for a further 30 minutes and is then cooled to −78° and a solution of 2.15 g of methyl 5-chlorocarbonylvalerate in 5 ml of THF is added dropwise. After a further 30 minutes 30 ml of saturated citric acid solution are added and the mixture is worked up in the customary manner. This gives 2-oxa-4-(5-methoxy-carbonylpentanoyl)-6$\alpha$,-7$\alpha$-epoxy-1$\beta$H,5$\beta$H-bicyclo[3,3,0]octan-3-one (Ib).

Example 3

A mixture of 5.32 g of Ia and 0.5 g of sodium acetate in 12 ml of acetic acid is cooled to 12°–15°, and 5.7 g of 40% peracetic acid are added dropwise. The mixture is stirred for 2 days at 12°–15° and is diluted with 20 ml of water, and 2 g of sodium sulfite are added in small portions while the mixture is cooled to 10°–15° by means of ice. When a negative starch-KI paper test is obtained, the mixture is worked up further in the customary manner. This gives Ib.

Example 4

A mixture of 1 g of Ia and 10 ml of 10% methanolic KOH solution is stirred at 20° for 0.5 hour. The mixture is acidified with aqueous HCl and is worked up in the customary manner, and the resulting crude 2-oxa-4-(5-carboxypentanoyl)-1$\beta$H,5$\beta$H-bicyclo[3,3,0]oct-6-en-3-one is dissolved in 10 ml of pyridine, and 1 g of p-benzamidophenol, 1 g of dicyclohexylcarbodiimide and 0.1 g of p-toluenesulfonic acid are added, the mixture is allowed to stand for 1 day at 20° and is filtered and the filtrate is stirred into water, and the 2-oxa-4-(5-p-benzamidophenoxycarbonyl)-pentanoyl)-1$\beta$H, 5$\beta$H-bicyclo[3,3,)]oct-6-en-3-one which is precipitated is filtered off.

Example 5 (preparation of a heptanoic acid)

5 g of barium oxide are added to a solution of 2.66 g of Ia (crude product) in 10 ml of methanol and 10 ml of water, and the mixture is kept on a steam bath for 16 hours under nitrogen (pH=10). The mixture is filtered, the filter is rinsed with water and the filtrate is acidified to pH 2–3 with citric acid and extracted with methylene dichloride. The organic phase is allowed to stad for 16 hours and is extracted with NaHCO$_3$ solution. The aqueous phase is acidified to pH 5 with citric acid, and extracted with ethyl acetate, and the extract is worked up in the customary manner. This gives 6-oxo-7-(5α-hydroxy-2-cyclopenten-1α-yl)-heptanoic acid. Mass spectrum: m/e (—H$_2$O )=208.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A ketolactone of the formula

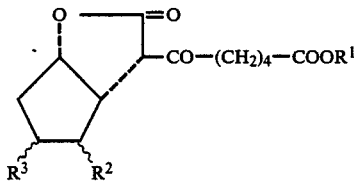

wherein
R$^1$ is H, C$_{1-6}$-alkyl or C$_{6-14}$-aryl or C$_{5-14}$-aryl substituted by methyl, fluoro, chloro, methoxy, acetamido or benzamido and
R$^2$ and R$^3$ together are an O atom or a single bond, or a salt thereof.

2. A ketolactone according to claim 1, wherein R$^1$ is H, methyl or ethyl.

3. A ketolactone according to claim 1, wherein R$^1$ is n-propyl, isopropyl, n-butyl, isobutyl, sec-butyl, tert-butyl, n-pentyl, isopentyl, hexyl, isohexyl, phenyl, tolyl, fluorophenyl, chlorophenyl, methoxyphenyl, acetamidophenyl or benzamidophenyl.

4. A ketolactone according to claim 3, wherein R$^1$ is p-benzamidophenyl.

5. 2-Oxa-4-(5-methoxycarbonylpentanoyl)-1βH,5βH-bicyclo[3,3,0]oct-6-en-3-3-one, a compound of claim 1.

6. 2-Oxa-6α,7α-epoxy-4-(5-methoxycarbonylpentanoyl)-1βH, 5βH-bicyclo[3,3,0]octan-3-one, a compound of claim 1.

7. 2Oxa-4-(5-p-benzamidophenoxycarbonyl pentanoyl)-1βH, βH-bicyclo-[3,3,0]oct-6-en-3-one, a compound of claim 4.

* * * * *